US007737118B2

(12) United States Patent
Demopulos et al.

(10) Patent No.: US 7,737,118 B2
(45) Date of Patent: *Jun. 15, 2010

(54) ROTATIONAL INTRATHECAL ANALGESIA

(75) Inventors: Gregory A. Demopulos, Mercer Island, WA (US); Pamela Pierce Palmer, San Francisco, CA (US)

(73) Assignees: Omeros Corporation, Seattle, WA (US); Regents of the University of California, Oakland, CA (US)

( * ) Notice: Subject to any disclaimer, the term of this patent is extended or adjusted under 35 U.S.C. 154(b) by 968 days.

This patent is subject to a terminal disclaimer.

(21) Appl. No.: 10/187,454

(22) Filed: Jul. 1, 2002

(65) Prior Publication Data

US 2003/0040486 A1 Feb. 27, 2003

Related U.S. Application Data

(63) Continuation of application No. PCT/US02/06721, filed on Feb. 28, 2002.

(60) Provisional application No. 60/302,796, filed on Jul. 2, 2001.

(51) Int. Cl.
*A61K 38/10* (2006.01)
*A61K 31/485* (2006.01)

(52) U.S. Cl. .......................... 514/13; 514/282

(58) Field of Classification Search ........................ None
See application file for complete search history.

(56) References Cited

U.S. PATENT DOCUMENTS

| 5,512,578 | A | 4/1996 | Crain et al. |
| 5,711,316 | A | 1/1998 | Elsberry et al. |
| 5,713,923 | A | 2/1998 | Ward et al. |
| 5,735,814 | A | 4/1998 | Elsberry et al. |
| 5,752,930 | A | 5/1998 | Rise et al. |
| 5,782,798 | A | 7/1998 | Rise |
| 5,798,114 | A | 8/1998 | Elsberry et al. |
| 5,814,014 | A | 9/1998 | Elsberry et al. |
| 5,820,589 | A | 10/1998 | Torgerson et al. |
| 5,821,219 | A | 10/1998 | Grandy et al. |
| 5,832,932 | A | 11/1998 | Elsberry et al. |
| 5,975,085 | A | 11/1999 | Rise |
| 5,978,702 | A | 11/1999 | Ward et al. |
| 6,071,925 | A | 6/2000 | Adam et al. |
| 6,075,034 | A | 6/2000 | Adam et al. |
| 6,113,527 | A | 9/2000 | Adam et al. |
| 6,172,067 | B1 | 1/2001 | Ito et al. |
| 6,262,066 | B1 | 7/2001 | Tulshian et al. |
| 6,277,384 | B1 | 8/2001 | Kaiko et al. |
| 6,340,681 | B1 | 1/2002 | Ito |

FOREIGN PATENT DOCUMENTS

| EP | 1 048 308 A2 | 11/2000 |
| WO | WO 97/40872 | 11/1997 |
| WO | WO 99/56803 | 11/1999 |
| WO | WO 00/66204 | 11/2000 |
| WO | WO 01/07050 A1 | 2/2001 |
| WO | WO 01/93852 A2 | 12/2001 |

OTHER PUBLICATIONS

Hassenbusch et al., Journal of Pain and Symptom Management, 27(6):540-563, Jun. 2004.*
Grisel et al., NeuroReport, 7:2125-2129, 1996.*
Aves, Kenneth E., "Parenteral Preparations," *Remington's Pharmaceutical Sciences*, Fifteenth Ed., 1975.
Wang, Yong-Xiang, et al., "Interactions of intrathecally administered ziconotide, a selective blocker of neuronal N-type voltage-sensitive calcium channels, with morphine on nociception in rats," *Pain*, 84;271-281 (2000).
Jenck et al., "A synthetic agonist at the orphanin FQ/nociceptin receptor ORL1: anxiolytic profile in the rat," *Proc. Natl. Acad. Sci. U.S.A.* 97:4938-4943 (2000).
Jhamandas et al., "Antinociceptive and morphine modulatory actions of spinal orphanin FQ," *Can. J. Physiol Pharmacol.* 76:314-324 (1998).
Dautzenberg et al., "Pharmacological characterization of the novel nonpeptide orphanin FQ/nociceptin receptor agonist Ro 64-6198: rapid and reversible desensitization of the ORL1 receptor in vitro and lack of tolerance in vivo," *J. Pharmacol. Exp. Ther.* 298:812-819 (2001).
Hao et al., "Lack of cross-tolerance between the antinociceptive effect of intrathecal orphanin FQ and morphine in the rat," *Neurosci. Lett.* 223:49-52 (1997).
Gouarderes et al., "Nociceptin receptors in the rat spinal cord during morphine tolerance," *Brain Res.* 838:85-94 (1999).
Xu et al., "Effects of intrathecal orphanin FQ on a flexor reflex in the rat after inflammation or peripheral nerve section," *Eur.J.Pharmacol.* 370:17-22 (1999).
Tian et al., "Endogenous orphanin FQ: evidence for a role in the modulation of electroacupuncture analgesia and the development of tolerance to analgesia produced by morphine and electroacupuncture," *Br. J. Pharmacol.* 124:21-26 (1998).
Ueda et al., "Enhanced spinal nociceptin receptor expression develops morphine tolerance and dependence," *J. Neurosci.* 20:7640-7647 (2000).

(Continued)

*Primary Examiner*—Marianne P Allen
(74) *Attorney, Agent, or Firm*—Marcia S. Kelbon

(57) ABSTRACT

A method of producing analgesia in a mammal is provided by rotational (alternating) intrathecal administration to the mammal of a pharmaceutically effective dose of at least one opioid receptor agonist, such as a μ-, δ-, or κ-opioid receptor agonist for a first period of time, followed by intrathecal administration to the mammal of a pharmaceutically effective dose of at least one opioid receptor-like receptor 1 (ORL-1) agonist for a second period of time. The intrathecal drug administration of the first and second periods of time may be repeated a plurality of times without attaining tolerance in the mammal to either drug. Implantable apparatus for rotational administration of the active agents is also disclosed.

4 Claims, 9 Drawing Sheets

OTHER PUBLICATIONS

Mogil et al., "The molecular and behavioral pharmacology of the orphanin FQ/nociceptin peptide and receptor family," *Pharmacol. Rev.* 53:381-415 (2001).

DeHaven-Hudkins et al., "Loperamide (ADL 2-1294), an opioid antihyperalgesic agent with peripheral selectivity," *J. Pharmacol. Exp. Ther.* 289:494-502 (1999).

Rizzi et al., "Effects of Ro 64/6198 in nociceptin/orphanin FQ-sensitive isolated tissues," *Naunyn Schmiedebergs Arch. Pharmacol.* 363:551-555 (2001).

Higgins et al., "Influence of the selective ORL1 receptor agonist, Ro64-6198, on rodent neurological function," *Neuropharmacology* 41:97-107 (2001).

Ogawa et al., "Synthesis and in vivo evaluation of [11C]methyl-Ro 64-6198 as an ORL1 receptor imaging agent," *Nucl. Med. Biol.* 28:941-947 (2001).

Calo' et al., "Pharmacological profile of nociceptin/orphanin FQ receptors," *Clin. Exp. Pharmacol. Physiol* 29:223-228 (2002).

Calo' et al., "The orphan receptor and nociception 9 RC 2," *Euroanesthesia* (2000).

Rover et al., "High-affinity, non-peptide agonists for the ORL1 (orphanin fq/nociceptin) receptor," *J. Med. Chem.* 43:1329-1338 (2000).

Shimada et al., "Effects of flurbiprofen on extracapsular cataract extraction," *Journal of the Eye* 4:719-722 (1987), English abstract.

Medtronic Inc., "About Advanced Pain Therapies (APT)," *Advanced Pain Therapies* (2002).

Chung et al., "The efficacy of intrathecal neostigmine, intrathecal morphine, and their combination for post-cesarean section analgesia," *Anesth.Analg.* 87:341-346 (1998) (Abstract only).

Yanez et al., "Intrathecal administration of morphine, midazolam, and their combination in 4 patients with chronic pain," *Rev. Esp. Anestesiol. Reanim.* 39:40-42 (1992) (Abstract only).

Corradini et al., "The putative OP(4) antagonist, [Nphe(1)]nociceptin(1-13)NH(2), prevents the effects of nociceptin in neuropathic rats," *Brain Res.* 905:127-133 (2001) (Abstract only).

Mogil et al., "Functional antagonism of mu-, delta- and kappa-opioid antinociception by orphanin FQ," *Neurosci. Lett.* 214:131-134 (1996) (Abstract only).

Tian et al., "Functional studies using antibodies against orphanin FQ/nociceptin," *Peptides* 21:147-150 (2000) (Abstract only).

Yamamoto et al., "Inhibitory effect of intrathecally administered nociceptin on the expression of Fos-like immunoreactivity in the rat formalin test," *Neurosci. Lett.* 284:155-158 (2000) (Abstract only).

Sakurada et al., "Nociceptin-induced scratching, biting and licking in mice: involvement of spinal NK1 receptors," *Br. J. Pharmacol.* 127:1712-1718 (1999) (Abstract only).

Grisel et al., "Orphanin FQ acts as a supraspinal, but not a spinal, anti-opioid peptide," *Neuroreport* 7:2125-2129 (1996) (Abstract only).

Tian et al., "Bidirectional modulatory effect of orphanin FQ on morphine-induced analgesia: antagonism in brain and potentiation in spinal cord of the rat," *Br. J. Pharmacol.* 120:676-680 (1997) (Abstract only).

Yamamoto et al., "Nociceptin/orphanin FQ: role in nociceptive information processing," *Prog. Neurobiol.* 57:527-535 (1999) (Abstract only).

Okuda et al., "Pharmacological profiles of J-113397, a novel nociceptin (orphanin FQ) antagonist in pain regulation," *Society for Neuroscience Abstracts* 26 (2000) (Abstract only).

Sutters et al., "Analgesic synergy and improved motor function produced by combinations of mu-delta- and mu-kappa-opioids," *Brain Res.* 530:290-294 (1990).

Miaskowski et al., "Kappa- and delta-opioid agonists synergize to produce potent analgesia," *Brain Res.* 509:165-168 (1990).

Inoue et al., "Pronociceptive effects of nociceptin/orphanin FQ (13-17) at peripheral and spinal level in mice," *J. Pharmacol. Exp. Ther.* 299:213-219 (2001) (Abstract only).

Smith et al., "Lack of cross-tolerance between intrathecal AM336 and intravenous morphine incontrast to the marked cross-tolerance between ziconotide and morphine," *Australian Society of Clinical and Experimental Pharmacologists and Toxicologi* (2000) (Abstract only).

Stoelting, R. K., "Intrathecal Morphine—An Underused Combination for Postoperative Pain Management," *Anesth Analg* 68:707-9 (1989).

Remington's Pharmaceutical Sciences, Fifteenth Edition (1975), p. 1461.

Wang, Y.-X., et al., "Interactions of Intrathecally Administered Ziconotide, a Selective Blocker of Neuronal N-type Voltage-sensitive Calcium Channels, with Morphine on Nociceptin in Rats," *Pain* 84:271-281 (2000).

Laudenbach, V., et al., "Nociceptin-Orphanin FQ Exacerbates Excitotoxic White-matter Lesions in the Murine Neonatal Brain," *J Clin Invest* 107:457-466 (2001).

Cheng, C.J-C., et al., "Either Sufentanil or Fentanyl, in Addition to Intrathecal Bupivacaine, Provide Satisfactory Early Labour Analgesia," *Canadian Journal of Anesthesia* 48(6):570-574 (2001).

Bennett, G., et al., "Future Directions in the Management of Pain by Intraspinal Drug Delivery," *Journal of Pain and Symptom Management* 20(2):S44-S50 (2000).

Dahm, P.O., et al., "Intrathecal Infusion of Bupivacaine with or without Buprenorphine Relieved Intractable Pain in Three Patients with Vertebral Compression Fractures Caused by Osteoporosis," *Regional Anesthesia and Pain Medicine* 24(4):352-357 (1999). Abstract only.

Zaveri, N., et al., "Characterization of Opiates, Neuroleptics, and Synthetic Analogs at ORL1 and Opioiod Receptors," *European Journal of Pharmacology* 428:29-36 (2001).

Mercadante, S., "Opioid Rotation for Cancer Pain: Rationale and Clinical Aspects," *Cancer* 86:1856-66 (1999).

Matthes, H.W.E., et al. "Activity of the δ-Opioid Receptor is Partially Reduced, Whereas Activity of the κ-Receptor is maintained in Mice Lacking the μ-Receptor," *The Journal of Neuroscience* 18(18):7285-7295 (1998).

US 6,172,075, 01/2001, Adam et al. (withdrawn)

* cited by examiner

ROTATIONAL INTRATHECAL ANALGESIA

CROSS REFERENCE TO RELATED APPLICATIONS

This application is a continuation of International Application No. PCT/US02/06721 filed Feb. 28, 2002 designating the United States, priority of which is claimed under 35 USC §120, and also claims the benefit of U.S. Provisional Application No. 60/302,796 filed Jul. 2, 2001, under 35 USC §119.

FIELD OF THE INVENTION

The present invention relates to methods and apparatus for the administration of intrathecal analgesics to achieve pain relief while delaying the onset of drug tolerance.

BACKGROUND OF THE INVENTION

In mammals, the receptors that respond selectively to noxious stimuli are known as nociceptors. Two distinct sets of peripheral sensory neurons are primarily responsible for the sensation of pain. The first, Aδ-nociceptive neurons, contain myelinated axons and are aroused primarily by noxious heat and mechanical stimuli. The second set of nociceptive neurons, which possess unmyelinated axons and are known as C fibers, are activated by high intensity, mechanical, chemical and thermal stimulation. Each of these sets of neurons has their cell bodies in the dorsal root ganglia. Their processes are pseudounipolar, with one axon that terminates in the periphery and one that terminates on neurons in the dorsal horn of the spinal cord.

Analgesia is the loss of sensitivity to pain without loss of consciousness. In recent years, the convergence of various lines of research demonstrates that analgesia can be produced by exogenous opioids, such as morphine, or endogenous opioids. This research has resulted in a model that explains the mechanism whereby pain is inhibited. See, for example, Kelly, D., "Central Representations Of Pain and Analgesia", *Principals of Neural Science*, Kandel and Schwartz, Eds. (1985).

The first means known to man for inducing analgesia was through the use of plant-derived opioid narcotics such as morphine. Postsynaptic opioid receptors have been characterized and include the following three basic subtypes: mu (µ), delta (δ) and kappa (κ). Endogenous opioids that bind these opioid receptors and thereby produce analgesia include the met- and leu-enkephalins, as well as β-endorphin. Most of the clinically used opiates, such as morphine, activate the µ-opioid receptor subtype.

Stimulation of C-fiber primary afferent neurons associated with pain results in the release of the potent neuropeptides substance P, calcitonin gene related peptide (CGRP) and somatostatin, as well as the "fast" neurotransmitter glutamate. The activated enkephalinergic inhibitory neurons in turn exert presynaptic inhibitory control over the release of these neurotransmitters, thus blocking the sensation of pain.

Opioid compounds (opiates) such as morphine, while effective in producing analgesia for many types of pain, are not always effective since the development of tolerance occurs in most patients. The development of tolerance to the effects of opioids is one of the major problems in chronic pain management today. Regardless of the route of opioid delivery, patients complain of decreasing pain relief with time. Although recent studies suggest that constant delivery of opioids (e.g., infusion or transdermal patch) produces less tolerance than intermittent dosing (e.g., short-acting opioids, such as Vicodin) (Jhamandas, K H et al., "Spinal amino acid release and precipitated withdrawal in rats chronically infused with spinal morphine," *J Neurosci* 16:2758-2766 (1996); Ibuki T et al., "Effect of transient naloxone antagonism on tolerance development in rats receiving continuous spinal morphine infusion," *Pain* 70:125-132 (1997)), tolerance is still a significant issue. Recent studies with patients receiving chronic intrathecal opioids demonstrate that in some patients an increase in dose of up to 2-3 fold over a period of months is necessary to maintain adequate analgesic levels (Winkelmuller M et al., "Long-term effects of continuous intrathecal opioid treatment in chronic pain of nonmalignant etiology," *J Neurosurg* 85:458-467 (1996); Paice J A et al., "Clinical realities and economic considerations: efficacy of intrathecal pain therapy," *J Pain Symp Manage* 14:S14-26 (1997); Sallerin-Caute B et al., "Does intrathecal morphine in the treatment of cancer pain induce the development of tolerance?," *Neurosurgery* 42:44-49 (1998)). A recent study of the intra-operative use of remifentanil indicates that rapid (within hours) tolerance to this µ-opioid agonist can occur (Guignard B. et al., "Acute opioid tolerance: intraoperative remifentanil increases postoperative pain and morphine requirement," *Anesthesiology* 93:409-417 (2000)). Basic research on human cell lines indicates that a 30% reduction in µ-opioid receptor molecular signaling pathways occurs as early as 24 hours in culture with a µ-opioid agonist (Elliot J. et al., "Tolerance to 1µ-opioid agonists in human neuroblastoma SH-SY5Y cells as determined by changes in guanosine-5'-0-(3-[35S]-thio) triphosphate binding," *Br. J. Pharmacol.* 121:1422-1428 (1997)). However, most researchers would agree that tolerance develops more rapidly in rats than in humans. For example, many patients have been successfully treated with stable-dose morphine for more than six days (which is the time-course for the development of morphine tolerance in rats) without becoming completely tolerant to the analgesic effects of morphine.

While escalating opioid use is not only a medicolegal issue for many physicians, escalating intrathecal opioids can result in side effects, such as myoclonus (Glavina M J et al., "Myoclonic spasms following intrathecal morphine," *Anaesthesia* 43:389-390 (1988); De Conno F et al., "Hyperalgesia and myoclonus with intrathecal infusion of high-dose morphine," *Pain* 47:337-339 (1991)). This side effect does not usually occur if the dose of intrathecal opioids is limited to a morphine equivalent of 60-70 mg/day. Although most patients start at intrathecal doses of less than 5 mg/day, even a 2-fold increase per year results in toxic doses within four years. At high doses, these compounds additionally produce side effects, such as respiratory depression, which can be life-threatening. Opioid drugs also frequently produce physical dependence in patients. Dependence appears to be related to the dose of opioid taken and the period of time over which the subject takes it. For this reason, alternate therapies for the management of chronic pain are widely sought. In addition, compounds which serve as either a replacement for, or as an adjunct to, opioid treatment in order to decrease the dosage of analgesic compound required, have utility in the treatment of pain, particularly pain of the chronic, intractable type.

Non-opioid drugs, such as the non-steroidal anti-inflammatory drugs (NSAIDs) provide an alternative therapy for the treatment of pain. The mode of action of NSAIDs is believed to be through inhibition of cyclooxygenase, the enzyme responsible for biosynthesis of the prostaglandins. As analgesics, the NSAIDs lack many of the side effects on the CNS that are associated with the opioids and they do not result in the development of dependence. They are only effective, however, on low to moderate intensity pain, and are not generally useful for intense pain. In addition, they have undesirable side effects, including the propensity to induce gastric or intestinal ulceration as well as disturbances of platelet function.

Despite the wide range of analgesic substances available, still lacking are drugs and drug administration regimes that are effective in reducing severe pain without requiring dose escalation due to the development of tolerance.

SUMMARY OF THE INVENTION

It has now been discovered that a new treatment regimen, termed "rotational analgesia," helps delay the development of tolerance to intrathecal opioids. In one aspect of the present invention, a method of producing analgesia in a mammal is provided comprising alternating intrathecal administration to the mammal of a pharmaceutically effective dose of at least one opioid receptor agonist, followed by intrathecal administration to the mammal of a pharmaceutically effective dose of at least one opioid receptor-like receptor 1 (ORL-1) agonist. The periods of alternating administration of each agent may then be repeated as many times or cycles as desired. Each period of administration of the opioid receptor agonist or the ORL-1 agonist is designed to be insufficient in duration to induce significant tolerance in the mammal to either drug, thereby delaying the development of tolerance. In one embodiment of the invention the opioid receptor agonist is selected from μ-opioid receptor agonists, δ-opioid receptor agonists, κ-receptor agonists and mixtures thereof.

In other aspects, an implantable, non-invasive, rate-adjustable dual reservoir pump is provided for rotational intrathecal delivery of the opioid receptor agonist and ORL-1 agonist drugs of the present invention.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
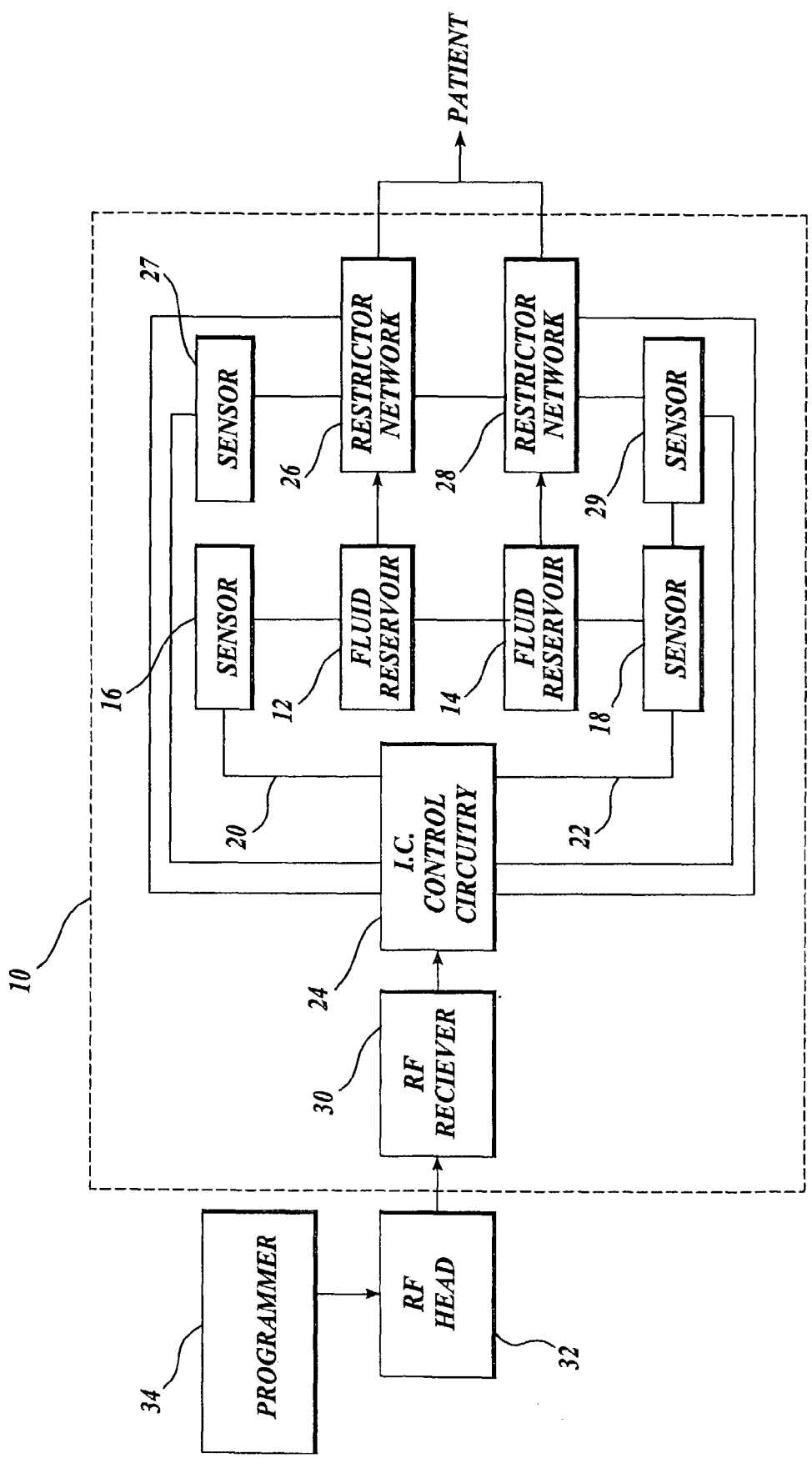
FIG. 1 is a schematic illustration in block diagram form of an implantable, rate-adjustable, dual reservoir pump system in accordance with the present invention.

In the practice of rotational analgesia, the administration of an intrathecal opioid drug is rotated with administration of another drug that has potent analgesic effects, but that exhibits minimal cross-tolerance with the opioid drug. To exhibit minimal cross-tolerance, for example, the opioid drug must not significantly bind to the rotational drug's receptor. Similarly, the rotational drug must not significantly bind to the opioid drug's receptor. Also of importance is that the overall effect on the pain pathways in the spinal cord are sufficiently similar that the patient does not go through withdrawal from the opioid during the rotation to the alternate drug. These two key factors limit the type of drug that can successfully be rotated with opioids in the practice of the invention. Consider receptor activation and second messenger system initiation as the early stage of the drug's effect and neuronal inhibition and decreased cyclic AMP levels as the late stages in the effect of the drug. Although not wishing to be bound by any particular theory, it is presently believed to be important that the rotated drugs have dissimilar early stages and highly similar late stages to avoid cross-tolerance, yet also avoid drug withdrawal. A presently preferred example of a drug that can be rotated successfully with an opioid drug in the practice of the invention is an ORL-1 agonist.

In one aspect the present invention relates to methods and apparatus for delaying the onset of tolerance in the administration of opioid and opioid-like receptor-1 (ORL-1) agonist drugs by rotating the administration of at least one opioid receptor agonist, such as a μ-opioid receptor agonist, a δ-opioid receptor agonist, a κ-opioid receptor agonist or mixtures thereof, with the administration of at least one ORL-1 agonist. Suitable opioid receptor agonists for administration in rotation with the at least one ORL-1 agonist include those opioid agonists that exhibit a minimal degree of cross-tolerance with the administered ORL-1 agonist, and that exhibit overall effects on the pain pathways in the spinal cord that are sufficiently similar to the effects exhibited by the administered ORL-1 agonist such that the patient does not go through withdrawal from the opioid agonist during the rotation to the ORL-1 agonist. As further described and illustrated by the Examples set forth herein below, μ-opioid receptor agonists and ORL-1 agonists can be beneficially administered in rotation in accordance with the present invention to extend duration to tolerance. It is also theorized that δ-opioid receptor agonists and/or κ-opioid receptor agonists may also be suitably rotated with ORL-1 agonists in accordance with the present invention, provided these opioid agonists are demonstrated to exhibit minimal cross-tolerance with ORL-1 agonists and similar effects on pain pathways.

In a first preferred embodiment of the invention, at least one μ-opioid receptor agonist is administered in rotation with at least one ORL-1 receptor agonist. The μ-opioid agonists, such as morphine, are rotated with an ORL-1 receptor agonist, such as nociceptin, since the μ-opioid receptor agonists do not bind to the ORL-1 receptor and nociceptin does not bind to μ-opioid receptors, therefore cross-tolerance is not likely (Hao J X et al., "Lack of cross-tolerance between the antinociceptive effect of intrathecal orphanin FQ and morphine in the rat," *Neurosci Lett* 223:49-52 (1997)). Both drugs decrease cyclic AMP levels and both are potent analgesics when applied intrathecally. Therefore, these two drug classes when administered intrathecally in accordance with the rotational intrathecal delivery regime of the present invention afford longer pain relief than when using either drug alone by delaying the onset of tolerance.

In other embodiments of the invention, at least one δ-opioid receptor agonist is administered in rotation with at least one ORL-1 receptor agonist. The intrathecal administration of orphanin FQ (nociceptin) had been observed to increase the duration of the antinociceptive response evoked by intrathecal administration of the δ-opioid receptor agonist deltorphin (Jhamandas, K H et al, "Antinociceptive and morphine modulatory actions of spinal orphanin FQ," *Can. J. Physiol. Pharmacol.* 76:314-324 (1998)). While the potential for exhibiting minimal cross-tolerance and similar effect on pain pathways needs to be determined in accordance with the present invention, it is theorized that δ-opioid receptor agonists may be useful for rotation with ORL-1 agonists.

In still other embodiments of the invention, at least one κ-opioid receptor agonist is administered in rotation with at least one ORL-1 receptor agonist. Again, the potential for minimal cross-tolerance and similar effect on pain pathways needs to be evaluated in determining the suitability for rotation of κ-opioid receptor agonists with ORL-1 agonists in accordance with the methods of the present invention.

Thus, in accordance with one aspect, the present invention provides a method of treating a mammal in need of analgesia comprising intrathecally administering to the mammal a pharmaceutically effective dose of either at least one opioid receptor agonist or at least one ORL-1 agonist for a first period of time, and intrathecally administering to the mammal a pharmaceutically effective dose of the other at least one opioid receptor agonist or at least one ORL-1 agonist for a second period of time (i.e., the analgesic agent not administered during the first period of time). In one embodiment, the second period of time serially follows the first period of time. In other embodiments, the end of the first period of time may overlap the beginning of the second period of time, and vice versa. The cycle of alternating intrathecal administration is preferably repeated for a plurality of treatment periods, for as long as desired in a particular application. If desired, the dosage level of drug being administered may be tapered down at the end of its administration period, while simultaneously tapering up the dosage level of the drug being rotated into the cycle, thereby providing a cross-over period during which both the opioid receptor agonist and the ORL-1 agonist are being administered to the mammal.

Suitable dosage levels for the opioid receptor agonists and the ORL-1 agonists of the invention will be determined by the prescribing physician depending on the needs of the patient, and include the dosage levels conventionally used for these analgesic agents, as is well known to those skilled in the art. For example, the μ-opioid receptor agonists may be administered at daily dosage levels of about 0.5 to about 25 mg/day, and more preferably at dosage levels of about 3 to about 20 mg/day. The ORL-1 agonists may be administered at daily dosage levels of about 1 to about 1,000 μg/day, more preferably about 5 to about 500 μg/day, and most preferably about 20 to about 100 μg/day. The daily dosage of the opioid receptor agonists or the ORL-1 agonists may be administered substantially continuously or intermittently.

Preferably, the first and second periods of administration for the opioid receptor agonists and the ORL-1 agonists are insufficient in duration to achieve significant tolerance in the patient to the analgesic effects of the administered drugs. As used herein, the term "tolerance" means a noticeable or measurable effect in the patient to become less responsive to the opioid receptor agonists or the ORL-1 agonists of the invention. Thus, a tolerance condition is characterized by the necessity to increase successive drug doses in order to produce identical analgesic effects, and by the apparent loss of potency of the drug observed during the course of successive administrations.

For example, the μ-opioid receptor agonist is preferably administered for a period of time insufficient to develop tolerance to the μ-opioid receptor agonist, such as for a period of from 1 to 30 days, more preferably from 1 to 20 days, and most preferably from 1 to 10 days, followed by administration of the ORL-1 agonist for a period of time insufficient to develop tolerance to the ORL-1 agonist, such as for a period of from 1 to 30 days, more preferably from 1 to 20 days, and most preferably from 1 to 10 days. The cycle of rotational intrathecal delivery of the μ-opioid receptor agonist followed by delivery of the ORL-1 agonist may then be repeated for similar periods of time, for as many cycles as desired, and is preferably repeated for at least a plurality of cycles. It is theorized that these same cycles may be suitable for rotation of δ-opioid receptor agonists or κ-opioid receptor agonists with ORL-1 agonists.

One common μ-opioid receptor agonist for use in the practice of the invention is morphine, although other μ-opioid receptor agonists may be used in the practice of the invention. Suitable μ-opioid receptor agonists for use in the practice of the invention include, for example, hydromorphone, fentanyl, sufentanil, methadone, meperidine and Try-D-Ala-Gly-[N-MePhe]-NH(CH$_2$)—OH ("DAMGO").

Potentially suitable δ-opioid receptor agonists may include, by way of example, deltorphin and [D-Pen$^2$, D-Pen$^5$] enkephalin ("DPDPE"). One exemplary κ-opioid receptor agonist that may be suitable for use in the present invention is (trans)-3,4dichloro-N-methyl-N[2-(1-pyrrolidynl)cyclohexyl]-benzene acetamide ("U-50,488H").

Suitable ORL-1 agonists for use in the practice of the invention include, for example, nociceptin (orphanin FQ) and other agents that bind to the ORL-1 receptor with high affinity, but that do not bind to the μ-opioid receptor with affinity sufficient to result in cross-tolerance. Depending on their binding properties, the following agents may potentially possess the required properties: Phepsi ([Phe$_1$psi(CH$_2$—NH)Gly$_2$]nociceptin-(1-13)-NH$_2$ (Chioce, *J. Biomed. Sci.* 7(3): 232-240 (2000))); (1S,3aS)8-(2,3,3a,4,5,6-hexahydro-1H-phenalen-1-yl)-1-phenyl-1,3,8-triaza-spiro[4,5]decan-4-one ("RO 64-6198") (Jenck F. et al., *PNAS* 97(9):4938-4943 (2000); and the 1-phenyl-1,3,8-triaza-spiro[4.5]decan-4-ones (Rover S., *J. Med. Chem.* 43(7):1329-1338 (2000)). Suitable ORL-1 agonists may be either peptidergic, e.g., nociceptin, or non-peptidergic, e.g., RO 64-6198.

Pharmaceutical compositions suitable for intrathecal injection may be sterilized solutions containing an effective amount of the compounds used according to the invention dissolved in a physiologically acceptable isotonic saline solution (for example, containing about 0.9% by wt. sodium chloride). Usually these solutions are adopted in a known manner to the physiological characteristics of the site of administration.

The analgesic agents of the invention may be administered intrathecally by any means known in the art. For example, intrathecal administration of the centrally acting analgesic agents of the invention may be accomplished via an externalized spinal catheter, a spinal catheter connected to an external infusion pump, a spinal catheter connected to a fully implanted infusion pump and other related systems known in the art to be therapeutically effective for the treatment of chronic pain. Direct intrathecal delivery of the analgesic agents is preferred to reduce systemic side effects caused by relatively high dosage systemic delivery. In this way, the active drugs are delivered in a concentrated manner and at low doses to their specific site of action on receptors in the neuraxis, minimizing systemic side effects as outlined above.

Implantable drug infusion devices may be used to provide patients with a constant or programmable long-term dosage or infusion of the analgesic agents of the invention. Such devices may be categorized as either active or passive.

Active drug or programmable infusion devices typically feature a pump or a metering system to deliver the drug into the patient's system. An example of such an active drug infusion device currently available is the SynchroMed™ programmable pump (Medtronic Incorporated, Minneapolis, Minn.). Such pumps typically include a drug reservoir, a peristaltic pump to pump out the drug from the reservoir, and a catheter port to transport the pumped out drug from the reservoir via the pump to a patient's anatomy. Such devices also typically include a battery to power the pump as well as an electronic module to control the flow rate of the pump. The SynchroMed™ pump further includes an antenna to permit the remote programming of the pump.

Passive drug infusion devices, in contrast, do not feature a pump, but rather rely upon a pressurized drug reservoir to deliver the drug. Thus such devices tend to be both smaller as well as cheaper as compared to active devices. An example of such a device includes the Medtronic IsoMed™ device (Medtronic Incorporated, Minneapolis, Minn.). This device delivers the drug into the patient through the force provided by a pressurized reservoir. In particular, this reservoir is pressurized with a drug to between 20 to 40 psi (1.3 to 2.5 bar) and is used to deliver the drug into the patient's system. Typically the flow path of the drug from the reservoir to the patient includes a flow restrictor, which permits a constant flow rate. The flow rate, however, is only constant if the pressure difference between reservoir and patient does not change. Factors that could impact this pressure difference include temperature, pressure-volume dependence of reservoir and altitude, among others. The selected pressure for the reservoir is thus typically quite high, so that absolute pressure changes only cause small and acceptable errors in flow rate. Suitable infusion pumps for use in the practice of the invention include the infusion pump disclosed in U.S. Pat. No. 5,820,589 of Medtronic, Inc., that is implantable and noninvasively programmable by means of radio frequency telemetry or other means of noninvasive telemetry. The disclosure of this patent is hereby incorporated herein by this reference.

In a presently particularly preferred embodiment, the analgesic agents of the invention may be administered by an implantable medical pump having at least two fluid reservoirs, one for the µ-, δ-, or κ-opioid receptor agonists of the invention and the other for the ORL-1 agonists of the invention, together with means for releasing the agonists from their respective reservoirs in an alternating manner in accordance with the rotational administration regime of the invention. In accordance with this aspect of the invention, the pump may comprise, for example:

(a) a first fluid reservoir for containing a first drug to be rotationally administered, e.g. the µ-, δ-, or κ-opioid receptor agonists of the invention;

(b) a regulator assembly adjustable to a plurality of flow rate settings for regulating the flow of fluid from the first fluid reservoir;

(c) a second fluid reservoir for containing a second drug to be rotationally administered, e.g., the ORL-1 agonists of the invention;

(d) a regulator assembly adjustable to a plurality of flow rate settings for regulating the flow of fluid from the second fluid reservoir; and (e) electromechanical control means for changing the passive regulator assemblies from a first flow rate setting to a second flow rate setting when the electromechanical control means receives an induced voltage in response to control signals, wherein the flow rate setting regulating the flow from the first fluid reservoir is set to zero when there is positive flow from the second fluid reservoir, and the flow rate setting regulating the flow from the second fluid reservoir is set to zero when there is positive flow from the first fluid reservoir, and wherein the electromechanical control means changes the flow rate settings from the first and second fluid reservoirs to zero in an alternating manner.

In accordance with this aspect of the invention, a drug infusion pump suitable for use in connection with the invention may comprise a first fluid reservoir, a second fluid reservoir and septums which serve, for example, as access ports to the reservoirs during the filling of the reservoirs with the first drug (e.g., µ-, δ-, or κ-opioid receptor agonists) and the second drug (e.g., ORL-1 agonists) of the invention, respectively, to be delivered to a specific desired location within a patient's body. If desired, the pump may further comprise a telemetry antenna or receiver preferably comprising a coil of wire within which a voltage may be induced when the receiver is in the presence of a transmitted signal. Such a signal is created, for example, by an assembly including a programmer operatively coupled to a radio frequency head disposed proximate to a pump implanted within the body of a patient near the skin.

The pump may further comprise a system that regulates the flow of fluid from the first reservoir and the second reservoir. Preferably, the flow regulating system comprises a valve network assembly adjustable to a plurality of flow rate settings, and includes a plurality of bi-stable valves that control the flow of fluid to a plurality of flow restrictors. The valves may be similar to, but not restricted to those described by Wagner, et al. See. Wagner, B. et al., "Bistable Microvalve with Pneumatically Coupled Membranes," *IEEE* 0-7803-2985-6/96, pp. 384-88, which is incorporated herein by reference. The restrictors may be similar to, but not limited to capillary tube technology used in the commercially available Infusaid and Anschutz fixed rate pumps. Alternatively, micro-machined etching technology can also be used to manufacture the restrictor.

In addition, the pump preferably comprises control circuitry for changing the state of one or more of the valves of the system in response to a received telemetry signal. The control circuitry preferably includes elements required to communicate with the transmitter, transform the signal from the transmitter to energy required to change valve states according to the telemetry received via the transmitter, and verify valve states and overall pump performance.

FIG. 1 shows a schematic illustration of an implantable rate-adjustable pump system in accordance with the present invention. As shown therein, the pump 10 preferably comprises a first fluid reservoir 12 for containing a solution of one of the analgesic agents of the invention, such as a solution of a µ-opioid receptor agonist, and a second fluid reservoir 14 for containing a solution of the rotated analgesic agent of the invention, such as a solution of an ORL-1 agonist. Sensors 16, 18 are provided for sensing fluid levels in the reservoirs 12, 14, respectively, and providing fluid level information along paths 20, 22 to integrated circuit controller 24. Fluid flow restrictors 26, 28 are provided for regulating the flow of analgesic agents from the first and second fluid reservoirs 12, 14 to a patient, at flow rates determined by controller 24 and sensors 27, 29. If desired, the pump system may be provided with an implantable RF receiver 30 adapted to receive signals from external RF transmitter 32 as set by a programmer 34, to regulate the flow patterns of analgesic agents from reservoirs 12, 14 in an alternating manner in accordance with the rotational intrathecal analgesic administration methods of the present invention.

Example 1

In Vivo Rat Hindpaw Withdrawal Latency (HWL) Study

Experiments were performed on male Sprague-Dawley rats having a weight of 200-250 g. The rats were housed in cages with free access to food and water. Room temperature was maintained at 24±2° C. and a 12 hr light/dark cycle was maintained. All experiments were conducted according to the guidelines of the Committee on Animal Research at the University of California at San Francisco. Every effort was made to minimize animal suffering.

Intrathecal Injections

A polyethylene catheter (Intramedic PE 10) was permanently implanted intrathecally with the inner tip at L3 to L5 in each animal. Rats displaying movement disorders following placement of the catheter were not used in the study. Injection volume was 10 µL of drug solution followed by 10 µL of 0.9% saline to flush the catheter. Intrathecal injections were performed every 12 hrs (morning and night).

In the morphine only group, 8 µg morphine HCl was injected every 12 hrs until complete tolerance developed and in the nociceptin only group, 10 nmol nociceptin was injected every 12 hrs until complete tolerance developed. These doses were chosen from previous studies that determined an equi-analgesic dosing for these two drugs. In the rotational analgesia group (shown as Morphine+Nociceptin in Tables 1 and 2, below), 8 µg morphine was injected every 12 hrs for the first two days, followed by 10 nmol nociceptin every 12 hrs for the next two days. The same pattern was repeated until complete tolerance developed.

Solutions for intrathecal injection were prepared with sterilized saline (0.9%). Nociceptin was obtained from Tocris, Balwin, Mo., morphine HCl was obtained from Shenyang First Pharmaceutical Factory, Shenyang, China.

Nociceptive Testing

The rats were trained with the testing conditions for five days prior to the experiments to decrease the stress response caused by handling and measurements and to obtain baseline responses. The hindpaw withdrawal latency (HWL) was measured for both thermal and mechanical stimulation. Thermal stimulation was achieved using the hot-plate test. The entire ventral surface of the rat's left or right hindpaw was placed on the hotplate, which was maintained at a temperature of 52° C. (51.8-52.2° C.). The Randall Selitto Test (UGO Basile, Type 7200, Italy) was used to assess HWL to mechanical stimulation. A wedge shaped probe with a loading rate of 30 g/second was applied to the dorsal surface of the manually handled hindpaw and the mechanical stimulation required to initiate the struggle response was assessed. The HWL is expressed in seconds, i.e., latency to withdrawal from the start of stimulation. The HWLs were measured 15 min after the second intrathecal injection on a daily basis.

Figure 2A:
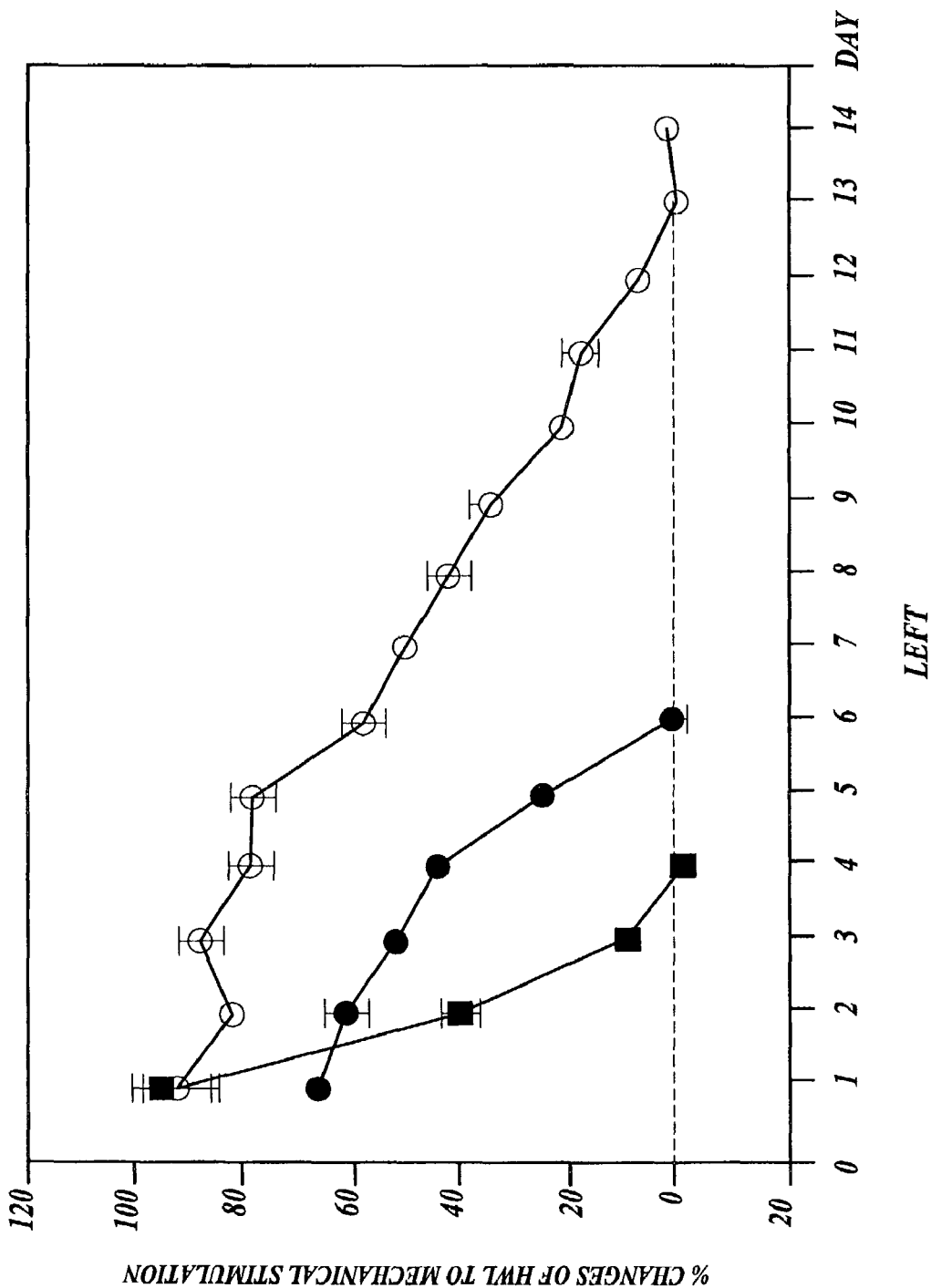
FIG. 2 is a graphical representation of the hindpaw withdrawal latencies (HWL) of rats to thermal (FIGS. 2A and 2B) and mechanical (FIGS. 2C and 2D) stimulation using intrathecal morphine (8 μg) alone (shown as ● in FIGS. 2A-2D), intrathecal nociceptin (10 nmol) alone (shown as ■ in FIGS. 2A-2D), or rotating morphine for 2 days, nociceptin for 2 days and then repeating the cycle (shown as ○ in FIGS. 2A-2D), as described in Example 1.
Figure 2B:
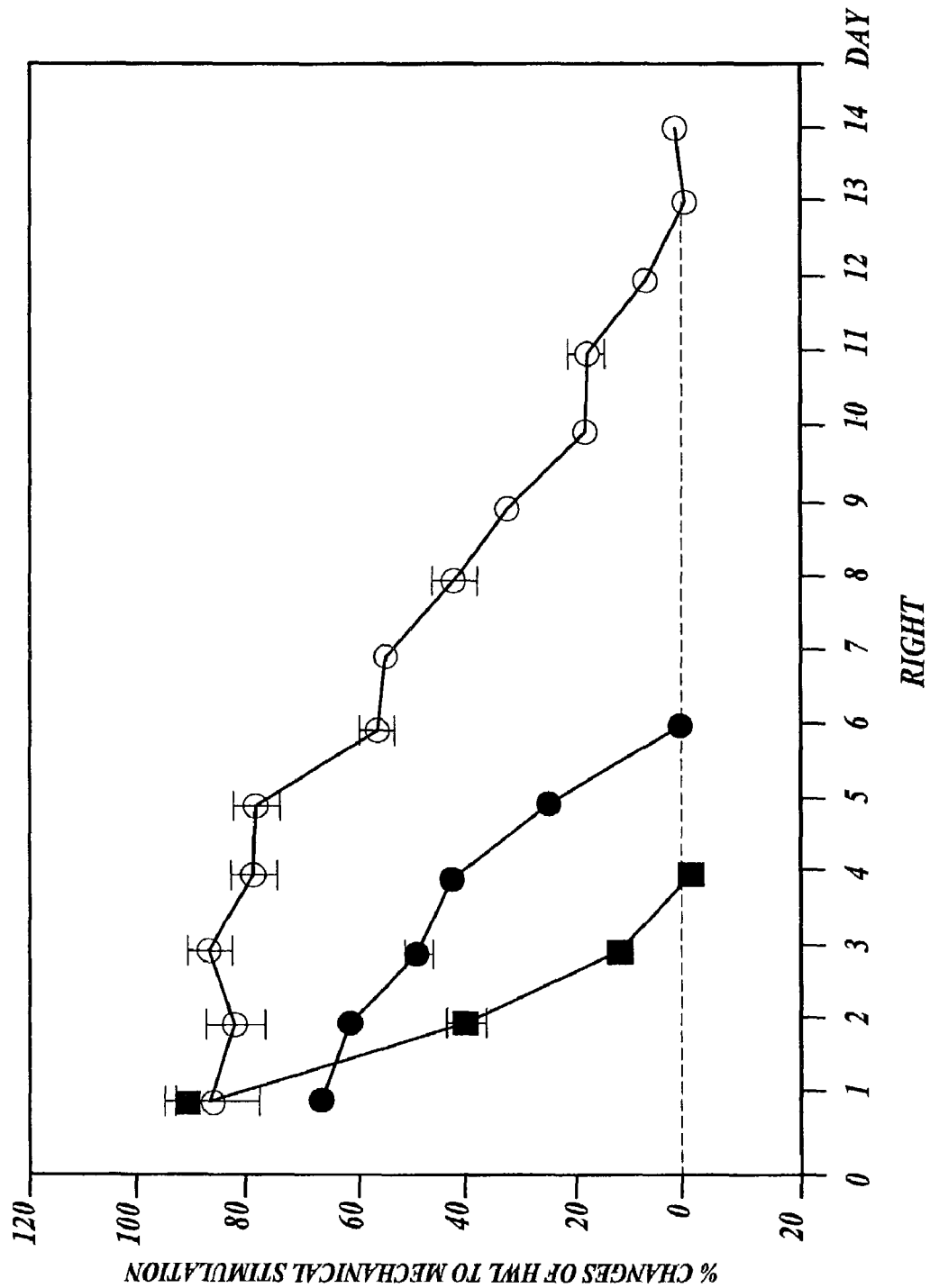

Data from the hindpaw withdrawal latency tests are presented in the following Tables 1 and 2 as average±standard error of the mean (SEM). The HWL to thermal (FIGS. 2A and 2B) and mechanical (FIGS. 2C and 2D) stimulation is expressed as percentage of the basal level for each rat. Each rat was tested with both types of stimulation.

TABLE 1

% Changes of HWL to Mechanical Stimulation
10 Minutes After Intrathecal Injection

| | Left | | | Right | | |
|---|---|---|---|---|---|---|
| Days | Morphine + Nociceptin | Morphine | Nociceptin | Morphine + Nociceptin | Morphine | Nociceptin |
| 1 | 44.77 ± 7.65 | 53.99 ± 2.96 | 69.90 ± 4.11 | 43.33 ± 7.19 | 56.04 ± 3.38 | 61.26 ± 3.85 |
| 2 | 37.91 ± 2.88 | 47.69 ± 2.54 | 31.28 ± 5.03 | 41.08 ± 3.81 | 46.74 ± 2.52 | 30.79 ± 6.58 |
| 3 | 41.56 ± 2.66 | 33.85 ± 1.60 | 10.59 ± 0.93 | 40.19 ± 1.33 | 33.44 ± 1.03 | 10.08 ± 1.05 |
| 4 | 37.81 ± 2.06 | 31.37 ± 2.02 | −0.62 ± 1.45 | 38.33 ± 1.53 | 28.84 ± 2.73 | −0.76 ± 2.32 |
| 5 | 38.47 ± 3.07 | 15.30 ± 1.39 | | 39.36 ± 2.84 | 16.54 ± 1.26 | |
| 6 | 33.95 ± 3.51 | 3.26 ± 1.86 | | 34.57 ± 1.99 | 2.72 ± 1.94 | |
| 7 | 33.90 ± 2.06 | | | 34.63 ± 2.06 | | |
| 8 | 30.97 ± 1.77 | | | 32.17 ± 2.08 | | |
| 9 | 28.36 ± 1.38 | | | 28.28 ± 1.32 | | |
| 10 | 20.09 ± 2.32 | | | 18.67 ± 1.00 | | |
| 11 | 12.34 ± 2.26 | | | 10.86 ± 3.00 | | |
| 12 | 3.71 ± 1.81 | | | 3.61 ± 2.48 | | |
| 13 | −1.12 ± 0.99 | | | −2.19 ± 1.15 | | |
| 14 | −0.61 ± 1.86 | | | −0.84 ± 1.61 | | |

TABLE 2

% Changes of HWL to Thermal Stimulation
10 Minutes After Intrathecal Injection

| | Left | | | Right | | |
|---|---|---|---|---|---|---|
| Days | Morphine + Nociceptin | Morphine | Nociceptin | Morphine + Nociceptin | Morphine | Nociceptin |
| 1 | 91.61 ± 7.98 | 66.26 ± 2.20 | 93.49 ± 3.77 | 85.14 ± 8.32 | 66.66 ± 1.51 | 90.42 ± 2.65 |
| 2 | 81.17 ± 1.86 | 61.25 ± 3.05 | 39.91 ± 3.66 | 80.68 ± 4.62 | 63.11 ± 0.64 | 43.02 ± 2.12 |
| 3 | 86.94 ± 3.42 | 51.66 ± 1.73 | 9.46 ± 2.31 | 85.40 ± 3.69 | 48.74 ± 2.40 | 12.01 ± 1.48 |
| 4 | 77.48 ± 3.10 | 43.63 ± 1.38 | −2.18 ± 2.07 | 79.15 ± 2.74 | 42.45 ± 1.70 | −3.67 ± 1.61 |
| 5 | 77.25 ± 3.05 | 23.85 ± 1.03 | | 79.79 ± 4.65 | 25.07 ± 2.07 | |
| 6 | 57.12 ± 3.64 | −1.30 ± 2.36 | | 56.40 ± 2.84 | 0.51 ± 1.61 | |
| 7 | 49.64 ± 1.37 | | | 54.01 ± 1.89 | | |
| 8 | 41.54 ± 3.60 | | | 42.73 ± 3.58 | | |
| 9 | 33.07 ± 1.35 | | | 31.53 ± 2.06 | | |
| 10 | 20.08 ± 1.77 | | | 17.17 ± 1.85 | | |
| 11 | 16.78 ± 2.93 | | | 17.75 ± 2.57 | | |
| 12 | 6.28 ± 2.19 | | | 6.81 ± 2.77 | | |
| 13 | −1.25 ± 0.93 | | | −1.02 ± 0.84 | | |

Results

Figure 2C:
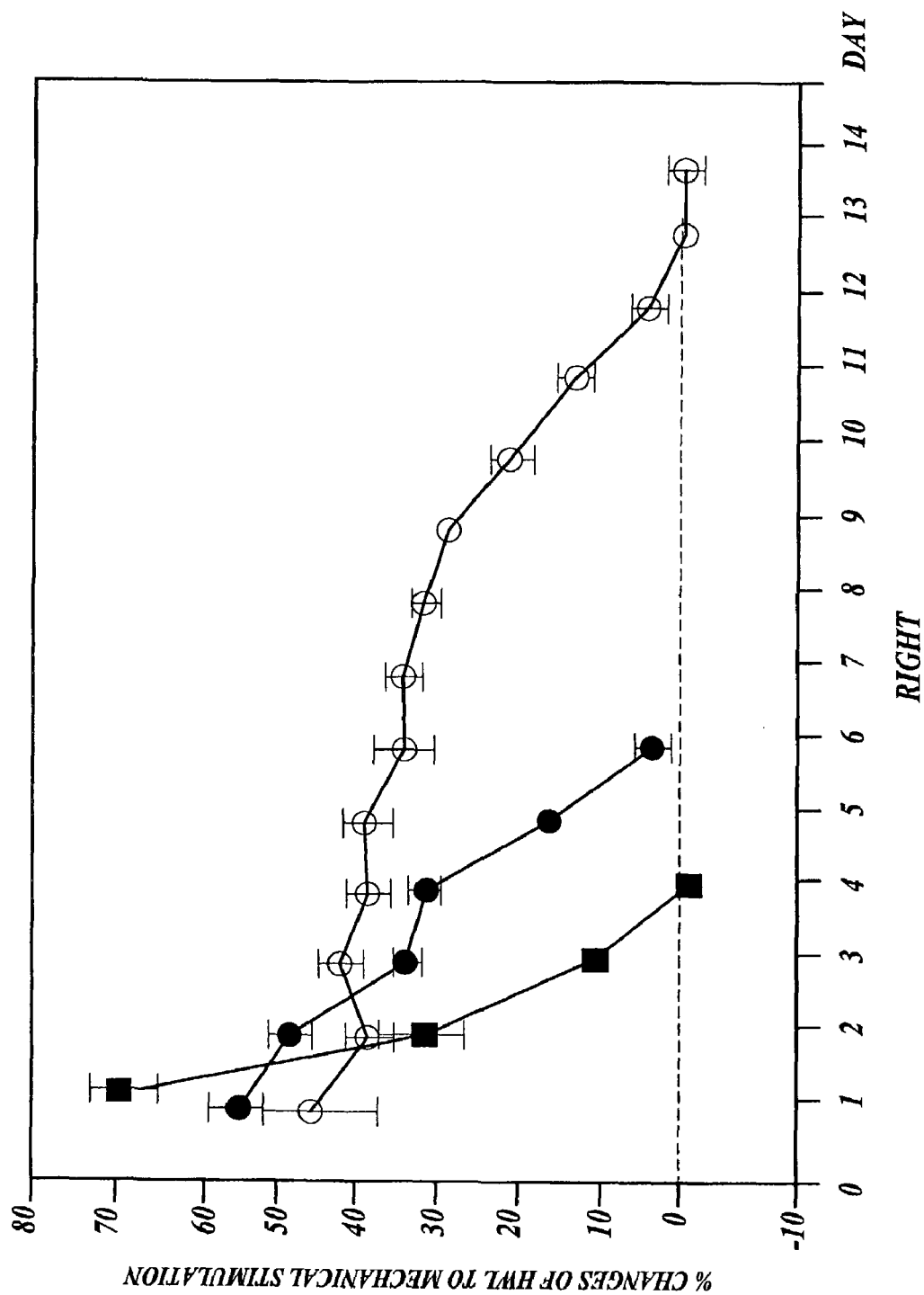
Figure 2D:
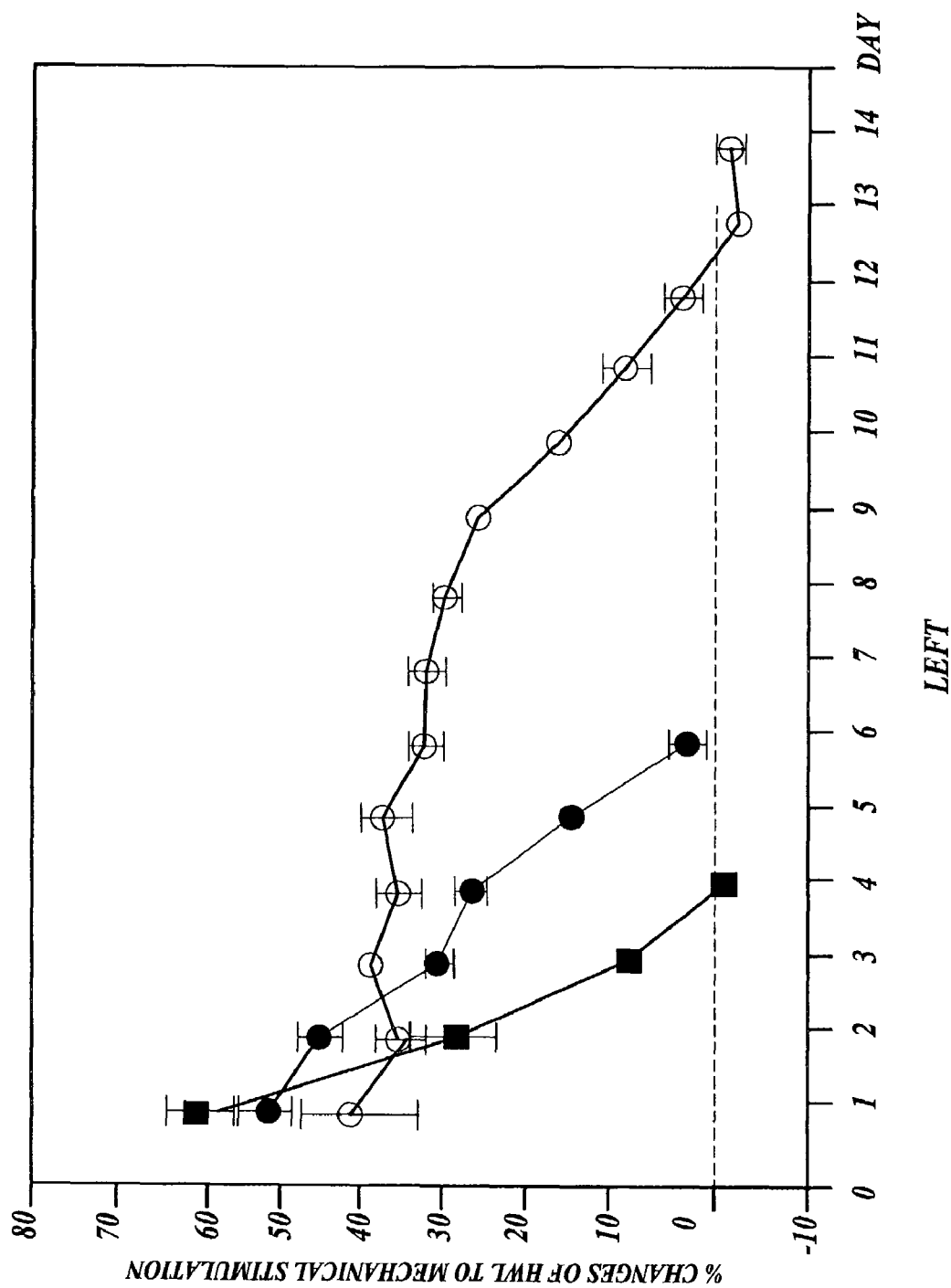
Figure 3A:
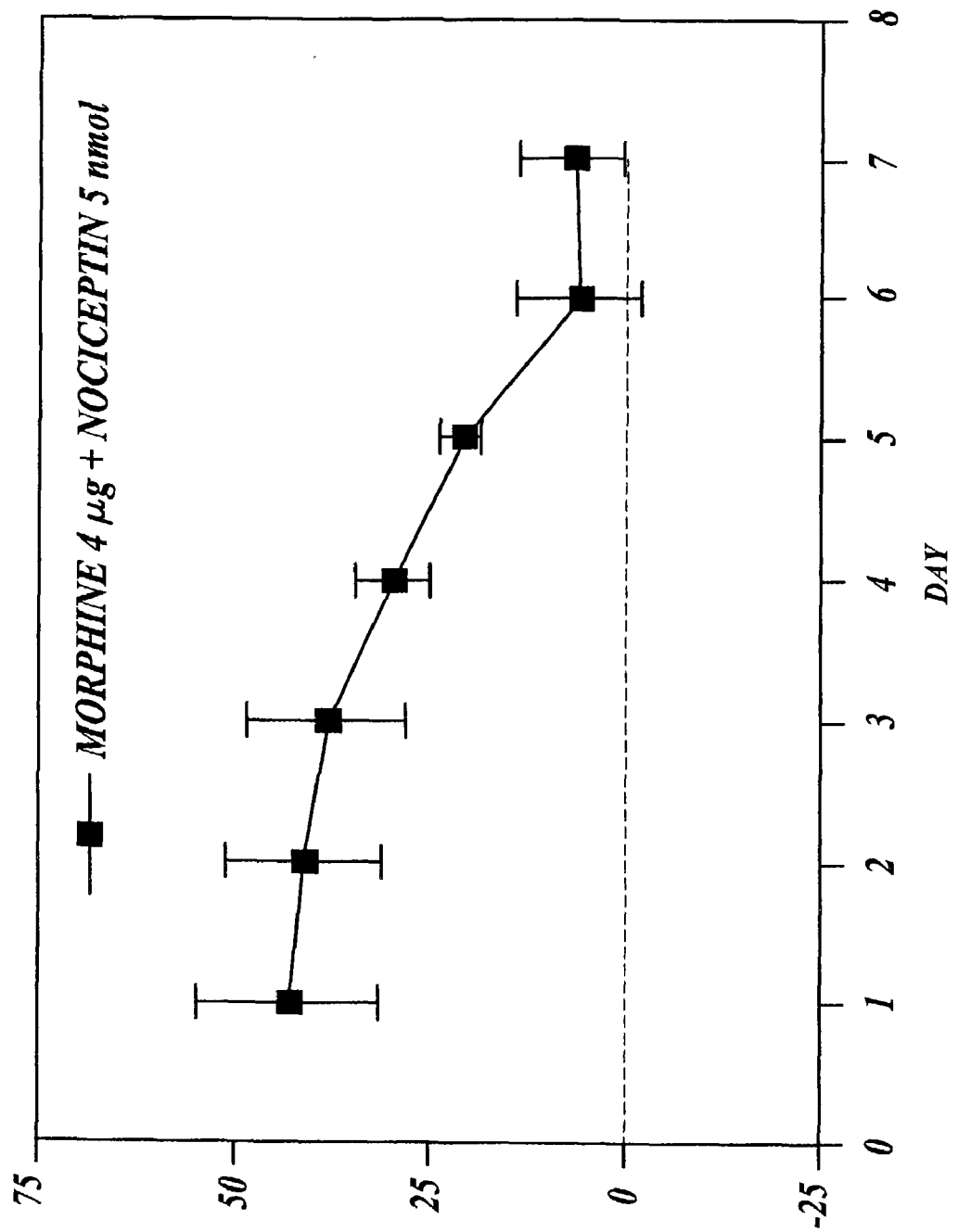
FIG. 3 is a graphical representation of HWL of rats to thermal (FIGS. 3A and 3B) and mechanical (FIGS. 3C and 3D) stimulation after twice daily administration of a combination of half-doses of morphine (4 μg) and nociceptin (5 nmol), as described in Example 2.
Figure 3B:
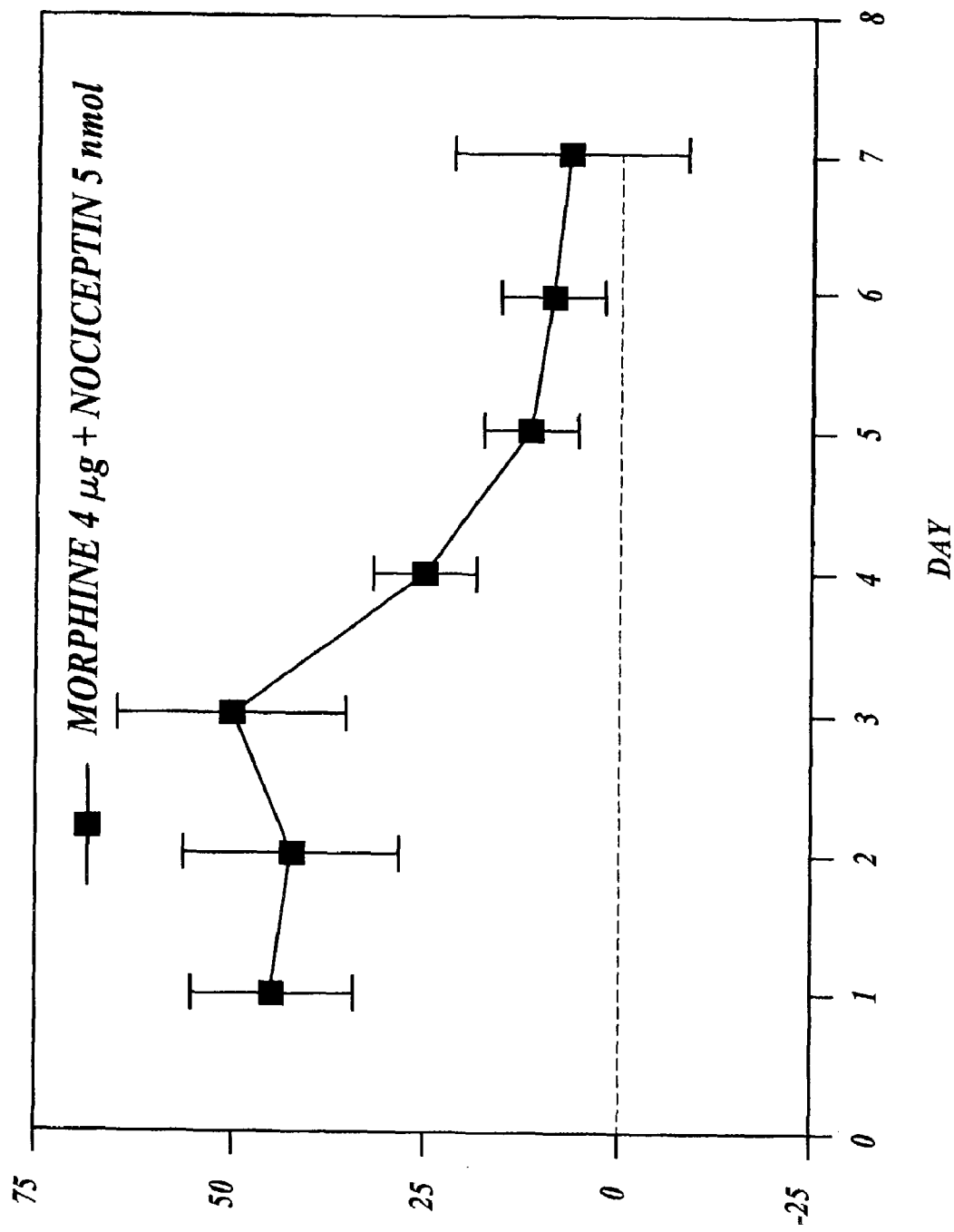
Figure 3C:
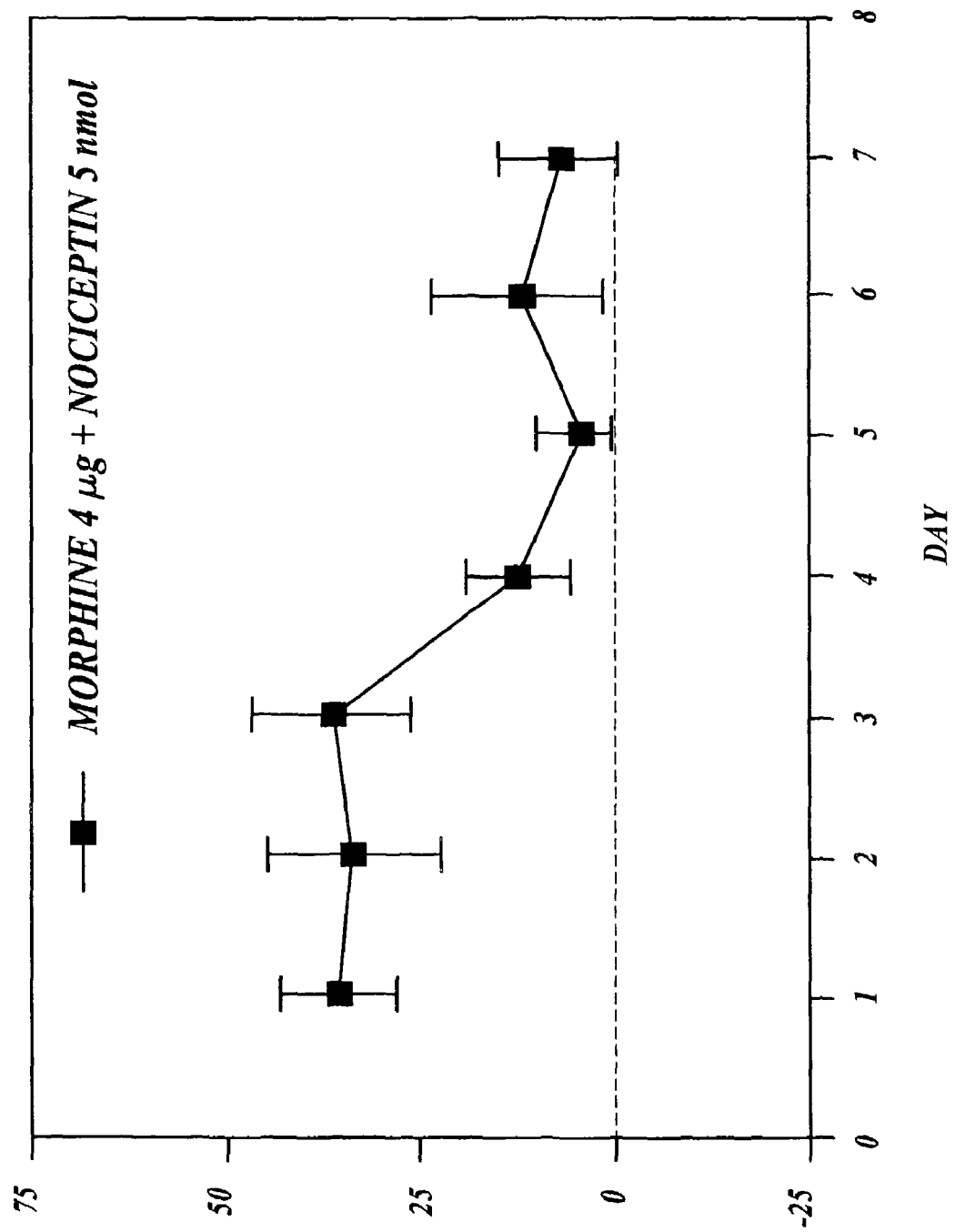
Figure 3D:
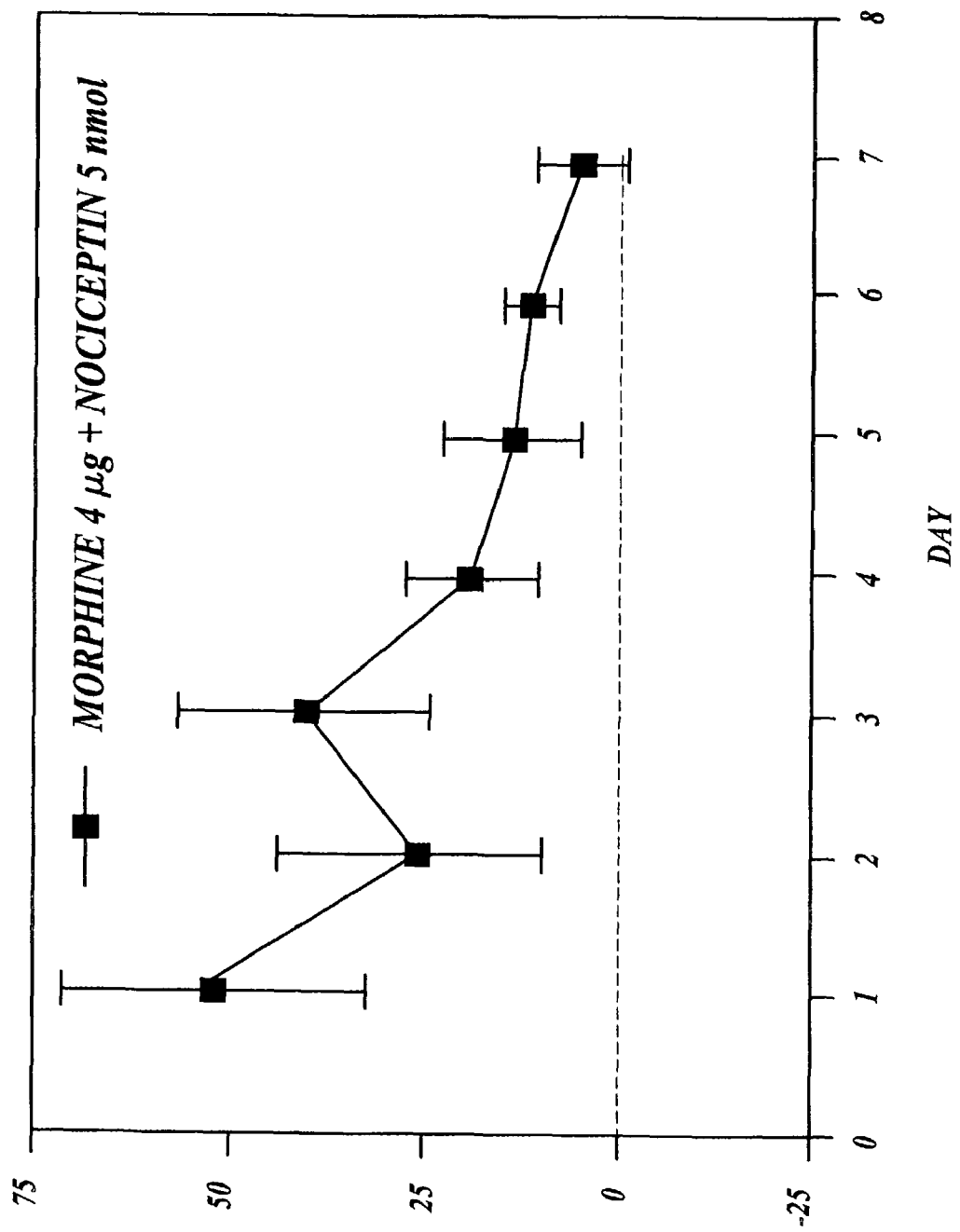

Morphine alone on day 1 produces an HWL increase of approximately 67% using thermal stimulation (FIGS. 2A and 2B) and 55% using mechanical stimulation (FIGS. 2C and 2D). Both right and left hindpaws had similar HWLs. Both mechanical and thermal HWLs gradually decrease with each successive day, such that by day 6 total tolerance to intrathecal morphine exists. Nociceptin alone on day 1 produces an HWL increase of approximately 90% using thermal stimulation (FIGS. 2A and 2B) and 60-70% using mechanical stimulation (FIGS. 2C and 2D). Both mechanical and thermal HWLs rapidly decrease with successive days, such that by day 4, complete tolerance to intrathecal nociceptin exists.

As shown in FIGS. 2A-2D, rotating morphine with nociceptin produces a dramatically different result. Whereas a similar decrease in HWL compared to the of morphine alone group between days 1 and 2 is measured, day 3 using nociceptin instead of morphine returns the HWL back to day 1 levels. Although tolerance is indeed observed for both medications with time, the time to complete tolerance is lengthened to 13 days. Similar time courses are observed for both hindpaws and for both types of simulation.

This example, as well as other reported studies in the literature, demonstrates that rats become completely tolerant to intrathecal morphine by day 6. By alternating equipotent doses of morphine and nociceptin intrathecally every two days (i.e., days 1 and 2 morphine, days 3 and 4 nociceptin, days 5 and 6 morphine, etc.), this example demonstrates that complete tolerance develops in 13 days, a greater than 100% increase in the length of time to complete tolerance compared with morphine alone and a greater than 200% increase compared to nociceptin alone. Interestingly, nociceptin tolerance is extremely rapid. In the nociceptin alone group, by day 2, 50% tolerance had already developed. This dramatic decrease in HWL is not seen on the second day of dosing nociceptin in the rotational analgesia group, (e.g., day 3 to day 4). Although not wishing to be bound by any particular theory, this decrease in nociceptin tolerance after treatment with morphine may be due to the upregulation of nociceptin receptors (ORL-1 receptors) in the dorsal horn of the spinal cord following intrathecal morphine treatment (Gouarderes C et al., "Nociceptin receptors in the rat spinal cord during morphine tolerance," *Brain Res* 838:85-94 (1999)). Because of the rapid development of tolerance, ORL-1 agonists may not be clinically useful as single agents intrathecally; however, by rotating a μ-opioid receptor agonist in accordance with the present invention, the development of ORL-1 agonist tolerance can be significantly lengthened. Although μ-opioid receptor agonists, such as morphine, are currently used as single agents intrathecally, the issues of tolerance and dose escalation are problematic clinically as mentioned earlier.

Example 2

Hindpaw Withdrawal Latency (HWL) Tests Using The Materials and Methods of

Example 1 for both thermal and mechanical stimulation were conducted on a group of eight rats that were treated by intrathecal injections of half-doses of morphine (4 μg) and nociceptin (5 nmol) every 12 hours. The results are shown in the following Table 3 and in FIGS. 3A-3D.

TABLE 3

| | % Changes of HWL | | | |
|---|---|---|---|---|
| | Thermal Stimulation | | Mechanical Stimulation | |
| Day | Left | Right | Left | Right |
| 1 | 43.31 ± 11.50 | 45.53 ± 10.33 | 35.17 ± 7.78 | 51.31 ± 20.07 |
| 2 | 41.28 ± 9.90 | 43.02 ± 14.04 | 33.12 ± 11.45 | 25.68 ± 17.32 |
| 3 | 38.53 ± 10.09 | 50.78 ± 14.80 | 35.90 ± 10.13 | 39.65 ± 16.61 |
| 4 | 30.32 ± 4.71 | 25.96 ± 6.96 | 11.68 ± 6.88 | 17.95 ± 8.54 |
| 5 | 21.63 ± 2.40 | 12.59 ± 6.18 | 3.52 ± 5.26 | 12.55 ± 8.98 |
| 6 | 6.40 ± 8.23 | 9.78 ± 6.65 | 11.19 ± 11.37 | 10.36 ± 3.75 |
| 7 | 7.14 ± 6.54 | 7.52 ± 15.23 | 6.16 ± 7.97 | 3.66 ± 6.27 |

Interestingly, by combining half-doses of intrathecal (IT) morphine and IT nociceptin, less total analgesia is obtained than with full doses of each drug administered individually. An average H increase of 40% is seen using thermal stimulation and an average 40% HWL increase is also seen with mechanical stimulation using the combination of IT drugs. Combining the two drugs does not appear to prolong tolerance development. Therefore, rotational administration is advantageous when compared to combinational administration.

Example 3

Prophetic Human Study

A test panel of five adult male humans suffering from high levels of chronic pain is treated by intrathecally administering 3 mg/day of morphine for a period of 7 days. On days 8 through 14, administration of the morphine is stopped and instead the panel is treated by intrathecal administration of 30 μg/day of nociceptin. On days 15 through 196, the treatment regimen of days 1 through 14 is repeated, rotating between intrathecal administration of morphine and nociceptin. Throughout the 196-day treatment regimen, a substantial reduction is obtained in the levels of experienced pain without significant tolerance development to either the morphine or nociceptin drugs.

In summary, rapid tolerance occurs to intrathecal morphine and very rapid tolerance occurs to intrathecal nociceptin. By rotating the intrathecal dosing of these agents in accordance with the present invention, the length of time to tolerance development is dramatically increased compared to each drug alone.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of producing analgesia in a human patient comprising alternating intrathecal administration to the patient of a pharmaceutically effective dose of morphine for a first time period of 1 to 30 days, followed by intrathecal administration to the patient of a pharmaceutically effective dose of nociceptin for a second time period of 1 to 30 days, wherein the first and second time periods are selected to maintain the analgesic effect in the patient produced by the morphine and the nociceptin and the administrations of the first and second periods of time are repeated for a plurality of treatment periods.

2. The method of claim 1 wherein the second period of time serially follows the first period of time.

3. The method of claim 1 wherein the first period of time is a period of from 1 to 10 days.

4. The method of claim 1 wherein the second period of time is a period of from 1 to 10 days.

* * * * *